(12) United States Patent
Washburn et al.

(10) Patent No.: US 8,303,502 B2
(45) Date of Patent: Nov. 6, 2012

(54) METHOD AND APPARATUS FOR TRACKING POINTS IN AN ULTRASOUND IMAGE

(75) Inventors: Michael Joseph Washburn, Brookfield, WI (US); Markus Wilhelm Marquart, Eching (DE); Todor Sheljaskow, Kenosha, WI (US)

(73) Assignee: General Electric Company, Schenectady, NY (US)

( * ) Notice: Subject to any disclaimer, the term of this patent is extended or adjusted under 35 U.S.C. 154(b) by 1413 days.

(21) Appl. No.: 11/714,550

(22) Filed: Mar. 6, 2007

(65) Prior Publication Data

US 2008/0221446 A1 Sep. 11, 2008

(51) Int. Cl.
*A61B 8/00* (2006.01)
(52) U.S. Cl. .................................. 600/437; 600/424
(58) Field of Classification Search .................. 600/407, 600/424, 437
See application file for complete search history.

(56) References Cited

U.S. PATENT DOCUMENTS

| | | | |
|---|---|---|---|
| 4,945,305 A | 7/1990 | Blood | |
| 6,063,030 A * | 5/2000 | Vara et al. | 600/437 |
| 6,214,029 B1 | 4/2001 | Thill et al. | |
| 6,216,029 B1 | 4/2001 | Paltieli | |
| 6,290,649 B1 | 9/2001 | Miller et al. | |
| 6,775,404 B1 | 8/2004 | Pagoulatos et al. | |
| 2007/0061726 A1* | 3/2007 | Rahn et al. | 715/719 |
| 2007/0276234 A1* | 11/2007 | Shahidi | 600/437 |
| 2008/0161688 A1* | 7/2008 | Poland | 600/437 |

FOREIGN PATENT DOCUMENTS

WO 2005039391 5/2005

OTHER PUBLICATIONS

Pagoulatos et al., Interactive 3-D Registration of Ultrasound and Magnetic Resonance Images Based on a Magnetic Position Sensor, IEEE Transactions on Information Technology in Biomedicine, vol. 3, No. 4, Dec. 1999, pp. 278-288.

* cited by examiner

*Primary Examiner* — Brian Casler
*Assistant Examiner* — Christopher Cook
(74) *Attorney, Agent, or Firm* — The Small Patent Law Group; Dean D. Small

(57) ABSTRACT

An ultrasound system comprises a position sensing module, an imaging tracking module, a display and a user interface. The position sensing module detects spatial information associated with a volume of data. The display displays first and second images based on the volume of data. The first and second images comprise first and second portions of the volume of data, and the first and second portions are at least partially different with respect to each other. The user interface selects a first image tracking point on the first image. The first image tracking point is indicated on the first image with a first indicator. The image tracking module tracks the first image tracking point within the volume of data. The image tracking module indicates on the display a spatial relationship of the first image tracking point to the second image.

21 Claims, 8 Drawing Sheets

METHOD AND APPARATUS FOR TRACKING POINTS IN AN ULTRASOUND IMAGE

BACKGROUND OF THE INVENTION

This invention relates generally to ultrasound imaging, and more particularly, to tracking points of interest within an ultrasound image.

Ultrasound is used for non-invasive diagnostic imaging and with invasive surgical techniques, such as biopsies and ablations. Typically, a user moves an ultrasound probe about a patient to acquire two-dimensional (2D) views, 3D and/or 4D volume representations of anatomy and items or structures of interest within the patient's body. However, there is currently no method to ensure proper accounting for each structure.

While scanning, there is often a need to count the number of structures, points, or items in the body, such as the number of nodules in the thyroid or the number of metastases in the liver. Unfortunately, it can be difficult to ensure that each occurrence or structure is counted exactly one time as the user navigates through an organ or other volume in the body. This is especially true when approaching the anatomy from multiple views to assure coverage or to improve imaging access of the tissue. As the imaging angle of the probe or the location of the probe on the patient changes, it is difficult to determine whether a structure that is currently visualized is newly identified, or has already been identified and counted. This may be increasingly complicated if there are many structures to count and may lead to a lower level of diagnostic confidence.

Once tissue is not within the current acquisition image or scanning plane and is no longer being displayed, the user must remember where the structures of interest are located within previously scanned anatomy. Often, the user has to search for the structure if the user wishes to go back to re-evaluate, image, perform additional investigation, and the like. This can be time-consuming and laborious, especially when there are many structures.

In another case, if the imaging of a structure is obstructed, such as by rib shadowing, the user will typically try to improve the image by moving the probe to view the structure from one or more different directions. If the structure is small, it may be difficult to detect, requiring additional time to locate and identify the structure from another view, or to determine that the structure may not be adequately viewed from that angle. It may be difficult to locate the structure of interest again when the user returns to the same original viewing angle. Improving the ability of the user to locate the structure of interest from multiple views would improve diagnostic confidence and improve efficiency.

Therefore, a need exists for identifying and tracking structures of interest within diagnostic images.

BRIEF DESCRIPTION OF THE INVENTION

In one embodiment, an ultrasound system comprises a position sensing module, an imaging tracking module, a display and a user interface. The position sensing module detects spatial information associated with a volume of data. The display displays first and second images based on the volume of data. The first and second images comprise first and second portions of the volume of data, and the first and second portions are at least partially different with respect to each other. The user interface selects a first image tracking point on the first image. The first image tracking point is indicated on the first image with a first indicator. The image tracking module tracks the first image tracking point within the volume of data. The image tracking module indicates on the display a spatial relationship of the first image tracking point to the second image.

In another embodiment, a method for tracking structures within a diagnostic imaging dataset comprises selecting a first image tracking point within a first image being displayed on a display. The first image is within a volumetric dataset comprising a reference coordinate system. A first graphical indicator is displayed on the first image and is associated with the first image tracking point. A relative position of the first image tracking point is tracked with respect to a subsequent image being displayed on the display. The relative position is based on the reference coordinate system. A second graphical indicator is displayed on the subsequent image based on the relative position of the first image tracking point to the subsequent image.

In yet another embodiment, an ultrasound system comprises a position sensing module and a position sensor. The position sensing module comprises a transmitter for creating a spatial detection field. The position sensor is mounted on an ultrasound probe and provides positional information with respect to the probe within the spatial detection field. The probe acquires at least a current acquisition image comprising ultrasound data and a display displays image tracking points within the ultrasound data. An image tracking module tracks the image tracking points with respect to the position sensor and the current acquisition image. The image tracking module changes graphical indicators associated with each of the image tracking points to convey a spatial relationship of the image tracking points to the current image.

DETAILED DESCRIPTION OF THE INVENTION

Figure 1:
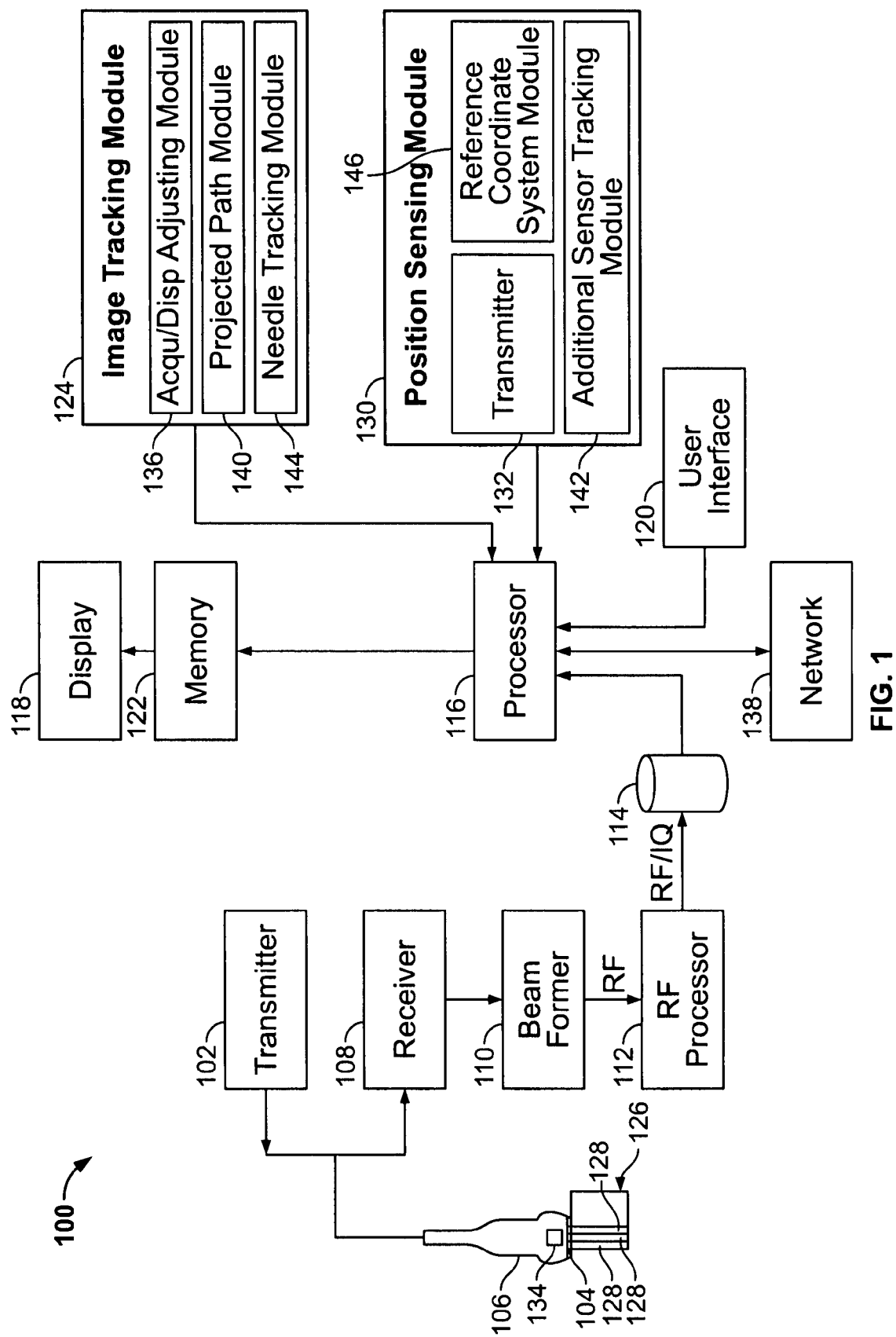
FIG. 1 illustrates a block diagram of an ultrasound system formed in accordance with an embodiment of the present invention.

The foregoing summary, as well as the following detailed description of certain embodiments of the present invention, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or random access memory, hard disk, or the like). Similarly, the programs may be stand alone programs, may be incorporated as subroutines in an operating system, may be functions in an installed software package, and the like. It should be understood that the various embodiments are not limited to the arrangements and instrumentality shown in the drawings.

FIG. 1 illustrates a block diagram of an ultrasound system 100. The ultrasound system 100 may be a cart-based or wheeled system, or may be much smaller in size, such as a hand-carried or handheld unit. The ultrasound system 100 includes a transmitter 102 that drives transducers 104 within a probe 106 to emit pulsed ultrasonic signals into a body. A variety of geometries may be used. The ultrasonic signals are back-scattered from structures in the body, like blood cells or muscular tissue within a patient 126, to produce echoes that return to the transducers 104.

The probe 106 may be moved, such as along a linear or arcuate path, while scanning the patient 126. At each linear or arcuate position, the probe 106 may obtain scan planes 128. Adjacent scan planes 128 may form a data slice, multiple data slices, or be combined to form a volume. Also, a volume representative of the patient 126 may be obtained by various techniques (e.g. 3D scanning, real-time 3D imaging or 4D scanning, volume scanning, 2D scanning with transducers having positioning sensors, freehand scanning using a Voxel correlation technique, 2D or matrix array transducers and the like).

The echoes are received by a receiver 108. The received echoes are passed through a beamformer 110, which performs beamforming and outputs an RF signal. The RF signal then passes through an RF processor 112. Alternatively, the RF processor 112 may include a complex demodulator (not shown) that demodulates the RF signal to form IQ data pairs representative of the echo signals. The RF or IQ signal data may then be routed directly to RF/IQ buffer 114 for temporary storage.

The ultrasound system 100 also includes a processor 116 to process the acquired ultrasound information (i.e., RF signal data or IQ data pairs) and prepare frames of ultrasound information for display on display 118. The processor 116 is adapted to perform one or more processing operations according to a plurality of selectable ultrasound modalities on the acquired ultrasound information. Acquired ultrasound information may be processed in real-time during a scanning session as the echo signals are received. Additionally or alternatively, the ultrasound information may be stored temporarily in RF/IQ buffer 114 during a scanning session and processed in a later or subsequent operation. Also, ultrasound information may be transferred to other systems, workstations, processors, and the like via network 138.

A user interface 120 allows an operator to enter data, enter and change scanning parameters, access protocols, measure structures of interest, and the like. The user interface 120 may comprise one or more of a rotating knob, switch, keyboard keys, mouse, touchscreen, light pen, or any other interface device or method known in the art.

A position sensing module 130 is within or attached to the ultrasound system 100, such as being provided within the processor 116 and may be implemented in hardware or software, or a combination thereof. The position sensing module 130 has a transmitter 132 that creates a spatial detection field proximate to the ultrasound system 100. The transmitter 132 may be configured as a magnetic, optical or other type of tracking device. The spatial detection field encompasses the patient 126 (or at least a portion of the patient 126 being imaged) and the probe 106. The size of the spatial detection field may be determined by the type or strength of the transmitter 132, and may be selected based on the desired application, for example, how far a sensor is expected to be from the transmitter 132.

A position sensor 134 is mounted on or within the probe 106. The position sensing module 130 tracks movements of the position sensor 134 within the spatial detection field, creating positional information within a reference coordinate system module 146. The reference coordinate system module 146 may be stored within the position sensing module 130 as an electronic file, database and the like. The reference coordinate system module 146 may be initialized by the user once the patient and ultrasound system 100 (or the transmitter 132) are in a desired scanning position with respect to each other. To maintain the reference coordinate system module 146, the patient 126 and the transmitter 132 remain in the same position relative to each other as the probe 106 (and the position sensor 134) move within the spatial detection field. If either the patient 126 or the transmitter 132 move relative to one another, however, the reference system may become invalid. An additional sensor tracking module 142 may be within the position sensing module 130 and/or stored within the memory 122. The additional sensor tracking module 142 may be used to track additional position sensors as discussed further below.

It should be understood that the arrangement of the position sensor 134 and the transmitter 132 are not limited to the embodiments illustrated. For example, a transmitter may be within and/or attached to the probe 106. A receiver may be located proximate to the system 100 and in communication with the system 100. Thus the creation of the spatial detection field is not limited to the configuration of the transmitter 132 and position sensing module 130 as discussed herein.

The ultrasound system 100 may continuously acquire ultrasound information at a frame rate that exceeds 50 frames per second—the approximate perception rate of the human eye. The acquired ultrasound information is displayed on the display 118 at a potentially slower frame-rate. A memory 122 is included for storing processed frames of acquired ultrasound information that are not scheduled to be displayed immediately. The memory 122 may comprise any known data storage medium, and may store other information as well, such as image and display processing algorithms and modules.

An image tracking module 124 may be provided within the processor 116 and may be implemented in hardware or software, or a combination thereof. One or more outputs of the image tracking module 124 may be stored within the memory 122. The image tracking module 124 accepts input from the user via the user interface 120 to identify one or more structures of interest within the patient 126 as the user views in-plane ultrasound data, or ultrasound information within the current scanning plane, image, or volume of the probe 106. The in-plane ultrasound data and in-plane view may also be referred to as a current acquisition image, and is not limited to scan planes, such as the scan planes 128. The user may also view cine data (e.g. a series of looping data) and frozen image data. As points or structures are identified by the user, the image tracking module 124 uses positional information acquired by the position sensing module 130 to determine and store location information of the structures of interest within the reference coordinate system module 146.

The image tracking module 124 also controls the type of graphical indicator used to identify structures and the relative locations of the identified structures with respect to the in-plane view, the current acquisition image of the probe 106, and/or the displayed image. Structures that are in-plane or within the displayed image are indicated with one or more in-plane indicators. Structures that have been identified and are not within the current acquisition image or displayed image are indicated with one or more out-of-plane indicators, which are different than the in-plane indicators. Shapes, such as crosses or plus signs, circles, squares, triangles, or other shapes may be used, as well as different colors to indicate the relative location of the structure with respect to the current acquisition or displayed image. Also, one or more of the size of the graphical indicator, the intensity, blinking rate, and the like may be varied to indicate positional information to the user. Optionally, the structures of interest may each be uniquely numbered within the displayed image, a total number of identified structures may be displayed on the display 118 proximate to the image, and the like. In addition, the image tracking module 124 allows the user to control whether some, all or none of the indicators are displayed on the display 118, such as to display only the in-plane indicators, without losing the positional data associated with the previously identified structures.

The image tracking module 124 may further provide the user the ability to classify one or more structures. For example, the user may wish to indicate the presence of a structure as well as to classify the structure based on size. For example, a first indicator may be used for structures that exceed a defined diameter or volume, and a second, different, indicator may be used for relatively smaller structures. The user may also indicate composition or type of lesion, such as solid or fluid-filled, or may indicate a desire for further investigation. Optionally, the user may add and/or edit a label that may be associated with and displayed proximate to a desired graphical indicator.

Acquisition/display adjusting module 136, projected path module 140, and needle tracking module 144 may be within the image tracking module 124 and/or stored separately within the memory 122. The modules 136, 140 and 144 provide additional acquisition, display, detecting and/or tracking functions with respect to user identified points and structures and are discussed further below.

Figure 2:
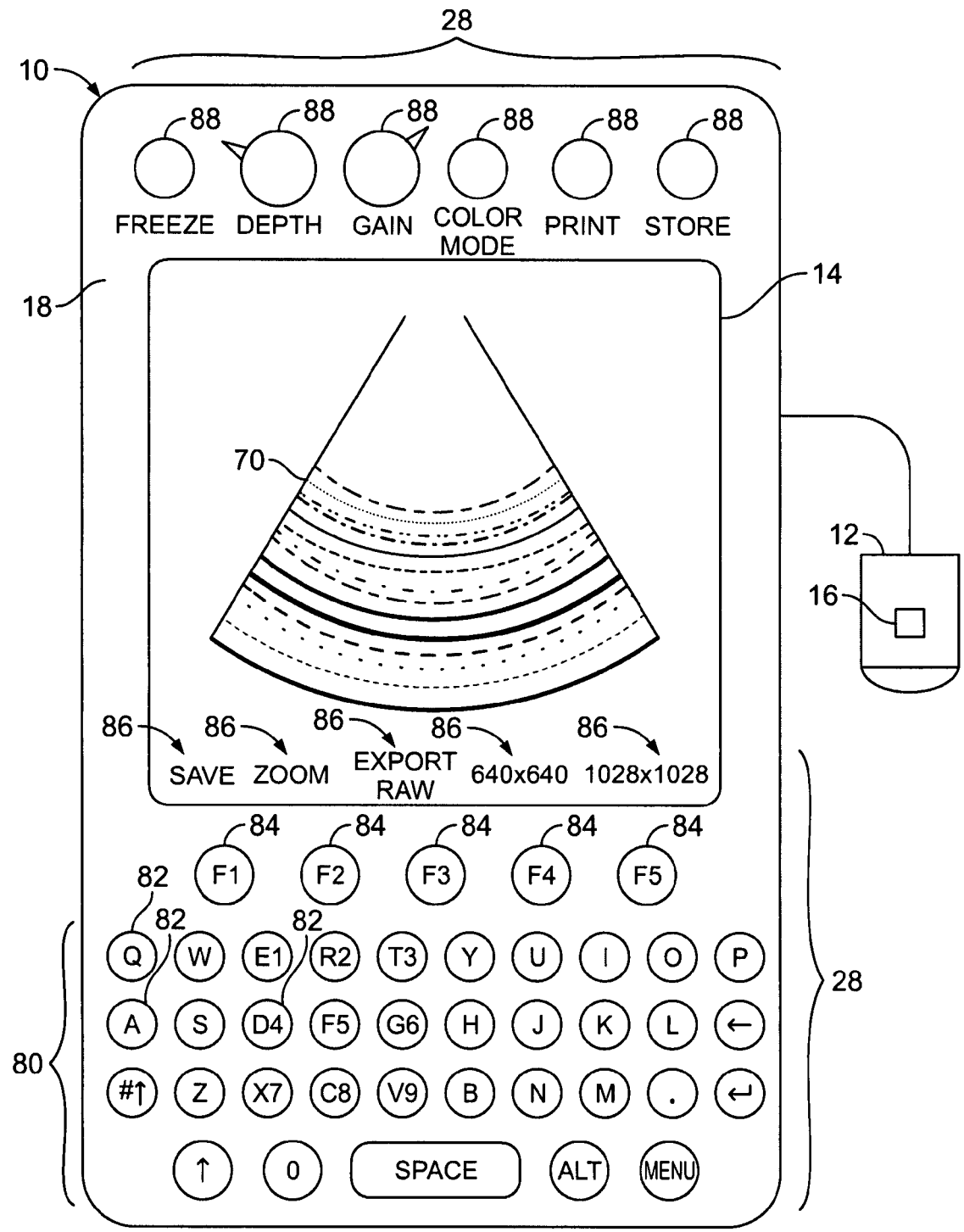
FIG. 2 is a pictorial drawing of an embodiment of a hand carried medical imaging device of the present invention.

FIG. 2 is a pictorial drawing of an embodiment of a hand carried medical imaging device 10 of the present invention. The hand carried medical imaging device 10 may also be referred to as handheld and portable. A probe 12 having a position sensor 16 mounted proximate thereto may be interconnected with the hand carried medical imaging device 10. A cover 18 may be provided for the hand carried medical imaging device 10, housing components there-within that provide the functionality of the image tracking module 124 (FIG. 1) and the position sensing module 130. Alternatively, a separate position sensing module 130 and/or transmitter 132 may be attached to, or provided proximate to, the cover 18.

Hand carried medical imaging device 10 includes the display 14, for example, a 320×320 pixel color LCD display (on which a medical image 70 may be displayed) and the user interface 28. In some embodiments of the present invention, a typewriter-like keyboard 80 of buttons 82 is included in user interface 28, as well as one or more soft keys 84 that may be assigned functions in accordance with the mode of operation of hand carried medical imaging device 10. A portion of display 14 may be devoted to labels 86 for soft keys 84. For example, the labels shown in FIG. 9 allow a user to save the current raw medical image data, to zoom in on a section of image 70 on display 14, to export raw medical image data to an external device or system, such as the system 100 of FIG. 1, or to display (or export) an image having a resolution of either 640×640 pixels or 1028×1028 pixels on an external device that includes a display. The device 10 may also have additional keys and/or controls 88 for special purpose functions, which may include, but are not limited to "freeze," "depth control," "gain control," "color-mode," "print," and "store."

Figure 3:
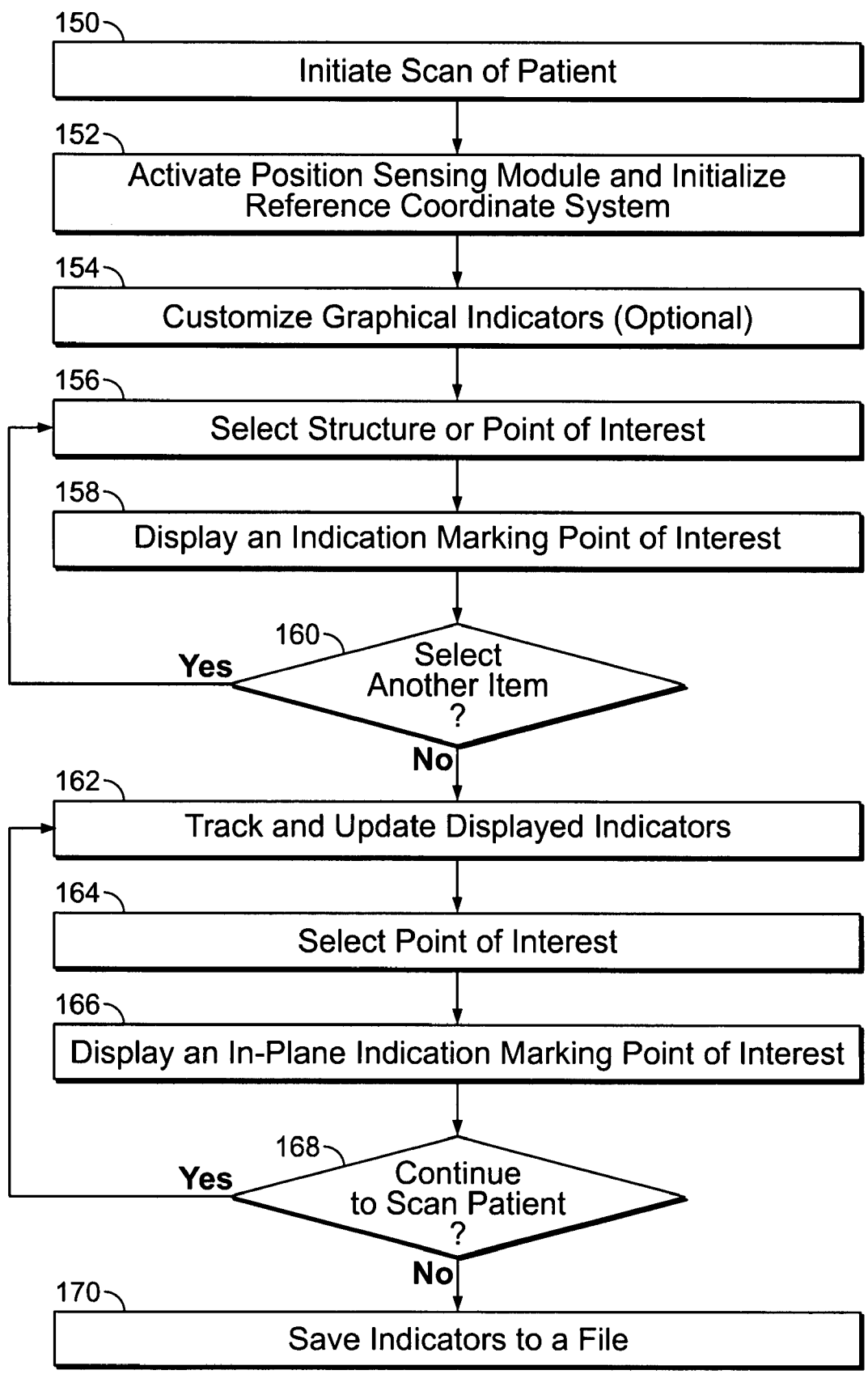
FIG. 3 illustrates a method for marking and tracking structures of interest within an ultrasound image in accordance with an embodiment of the present invention.

FIG. 3 illustrates a method for marking and tracking structures of interest within an ultrasound image. At 150, the user initiates an ultrasound scan of the patient 126 using the probe 106. The probe 106 may be any type of known probe, and is not limited to producing scan planes 128 or a volume as previously discussed. The position sensor 134 is mounted on or within the probe 106. At 152, the user may use the user interface 120 to activate the position sensing module 130 and initialize the reference coordinate system module 146. The transmitter 132 is activated, and records and tracks the position of the position sensor 134. Alternatively, the position sensing module 130 may be activated when the user selects a predetermined scanning protocol that makes use of image tracking points.

The graphical indicators may be predetermined, such as a first indicator for in-plane structures and a second indicator for out-of-plane structures. Optionally, at 154, the user may customize the graphical indicators to be used during the exam. For example, the user may wish to count nodules or other lesions within anatomy, and thus directs the image tracking module 124 to provide a total number of indicated lesions on the display 118, or to display each lesion along with a numerical indicator, such as 1, 2, 3, and so on. Also, the user may wish to activate options such as color coding or shape coding to identify lesions that are desirable to biopsy, or alternatively, avoid during in interventional procedure. Alternatively, the user may customize the display of a graphical indicator after an associated image tracking point is selected.

Figure 4:
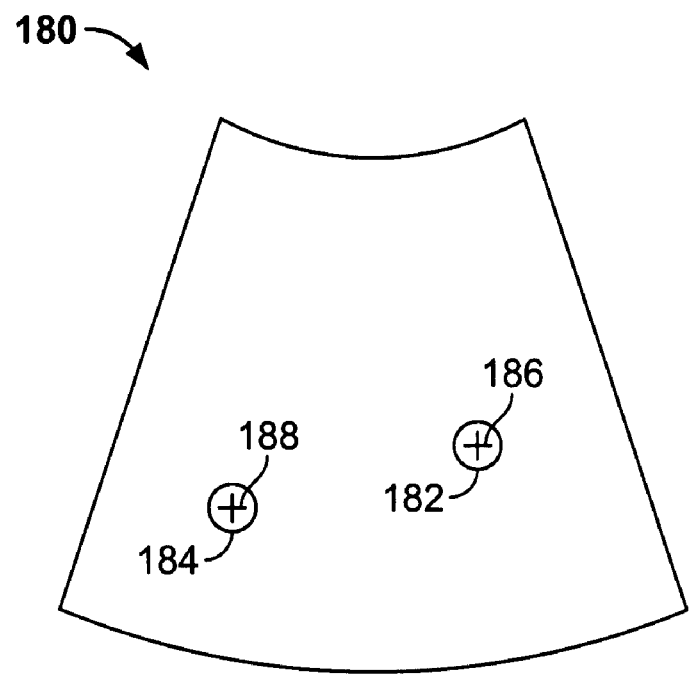
FIG. 4 illustrates an ultrasound image having first and second structures indicated with graphical indicators in accordance with an embodiment of the present invention.

FIG. 4 illustrates an ultrasound image 180 having first and second structures 182 and 184 that are indicated generically as circles. By way of example, the first and second structures 182 and 184 may be nodules within a thyroid of the patient 126 that are visible within the plane, volume, or slice currently being acquired by the probe 106, within a previously acquired volume, or within a frozen image.

At 156 of FIG. 3, the user selects a point within the ultrasound image 180 on the display 118, which may be a live in-plane image or may be frozen. The point is used to refer to a specific anatomical point within the image 180, or to identify a structure, anatomy or lesion of interest within the image 180. For example, the user may use a device provided within the user interface 120 such as a button, clicking with a mouse, or a touch screen. At 158, the image tracking module 124 places a graphical indicator at the selected image tracking point. For example, the user selects an image tracking point within the first structure 182 and the image tracking module 124 directs the display 118 to display in-plane indicator 186 at the image tracking point to indicate the position of the first structure 182. In this example, the in-plane indicator 186 is graphically represented as a "+". Positional information related to the point in space within the coordinate system is associated with the indicator and may be stored in the reference coordinate system module 146.

At 160, if the user wishes to select another structure or point, the method returns to 156. With the user interface 120, the user selects, for example, a point within the second structure 184. At 158, the image tracking module 124 displays in-plane indicator 188 on the display 118 at the selected point, and also associates the point in space selected at 158 with the particular graphical indicator, storing positional information, such as coordinate information indicating a spatial relationship within the spatial detection field, in the reference coordinate system module 146.

In this manner, the user may identify and display multiple image tracking points that indicate anatomical locations and/or structures of interest. The location of the point is graphically overlaid onto the current 2D or 3D image displayed on the display 118. Each of the image tracking points may be tracked by the image tracking module 124 with respect to each other, the in-plane image or other image or volume currently being displayed, and/or additional sensors and/or external structures such as a biopsy needle as discussed below. Therefore, the user may move the probe 106 on the patient 126 to view other anatomy, change direction or viewing angle, and the like, while the graphical projections of the points are maintained on the display 118.

Graphical indicators may be used to identify anatomy or structure other than with single points. For example, a line may be created by dragging a mouse along an area, or a line may be defined by a series of points. Also, a plane or a portion of a plane may be indicated, as well as a vessel or portion of a vessel, a volumetric graphical indicator may be used, and the like.

At 162, the image tracking module 124 tracks the positions in space of all of the image tracking points, using spatial relationship information from the position sensing module 130, and changes the appearance of the graphical projection(s) as needed to provide relative positional information to the user, such as how far each point is from the current acquisition image on the display 118, in what direction the image tracking point lies relative to the current acquisition image, and the type of image tracking point, as desired. Graphically, an image tracking point may be represented by a green cross when the image tracking point is in the current imaging plane. When the image tracking point is out-of-plane, the indicator may be a differently colored square, wherein the size and color of the square is used to convey positional information with respect to the in-plane image.

Figure 5:
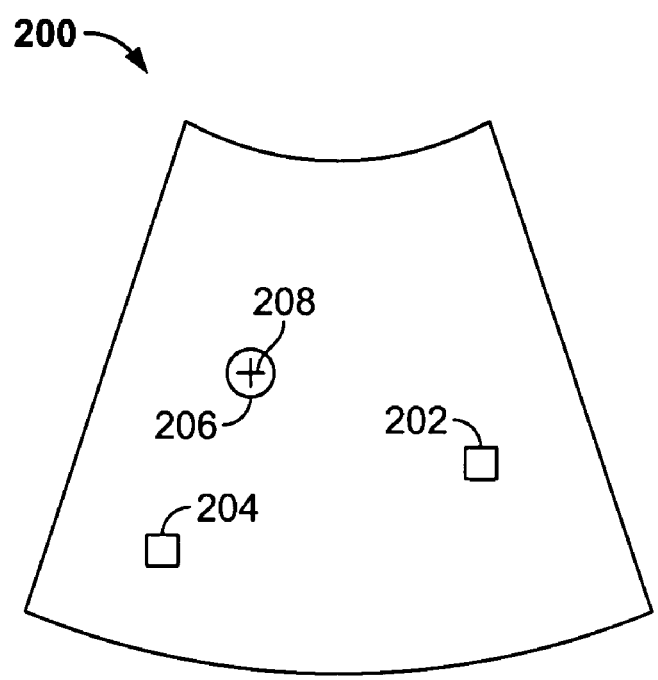
FIG. 5 illustrates an ultrasound image having graphical indicators indicating points that are outside of the in-plane image and a point within the in-plane image in accordance with an embodiment of the present invention.

FIG. 5 illustrates an ultrasound image 200 of the patient 126 having graphical indicators indicating points that are outside of the currently displayed image. Specifically, the first and second structures 182 and 184 of FIG. 4 are beyond the in-plane image of FIG. 5. Returning to 162 of FIG. 3, the image tracking module 124 changes the graphical indicators for the image tracking points identified in tissue areas outside the current image. The first and second in-plane indicators 186 and 188, indicated in FIG. 4 with "+" have been changed to first and second out-of-plane indicators 202 and 204, indicated with squares or boxes.

The first and second out-of-plane indicators 202 and 204 are projected onto the image 200. The graphical representations may provide an indication of being in-plane or out-of-plane, an indication of how far out-of-plane, an indication of which direction the image tracking point is out-of-plane with respect to the currently displayed image, and may provide an annotation to help distinguish between tracking points of the same style. Positional information related to the direction of being out-of-plane may be indicated by the color of the square, and the distance and/or relative distance from the in-plane image may be indicated by the size of the square and/or the intensity of the color. It should be understood that the graphical representations are not limited to those shown or discussed herein. Also, the user may customize how the relational information is communicated via the graphical indicators based on personal preference.

For points or structures that may be defined by indicators other than a single image tracking point, the same principle is applied, but the graphical representation may vary. For example, a line may be defined that extends through and beyond the current in-plane view. A green cross may be displayed at the intersection point(s). Along one direction, the line may be one color and color intensity may increase as the portion of the line extends further from the current view. A different color may be used to indicate the line extending in the other direction. The line may also be represented as a series of points. For a volumetric graphical indicator such as a sphere, rectangular or square box, or an asymmetric segmentation, the portion of the indicator that is in-plane may be indicated with a green boundary line or the image data within the volumetric indicator may be color-coded. When no portion of the volumetric indicator is in the current image, a representative outline and/or nearest point may be projected onto the current image.

At 164 of FIG. 3, the user selects a third structure 206 on the image 200 with the user interface 120, and at 166 the image tracking module 124 displays a third in-plane indicator 208 on the ultrasound image 200 on the display 118. The image tracking module 124 also stores an associated third image tracking point in the reference coordinate system module 146. At 168, if the user wishes to continue to scan the patient 126, the method returns to 162. If the scan is complete, at 170 the image tracking module 124 stores data related to the indicated points and/or structures that have been selected. For example, the data may be stored to the memory 122 with the patient data and any positional and/or spatial information needed to recreate the patient scan and image tracking points for future viewing.

Figure 6:
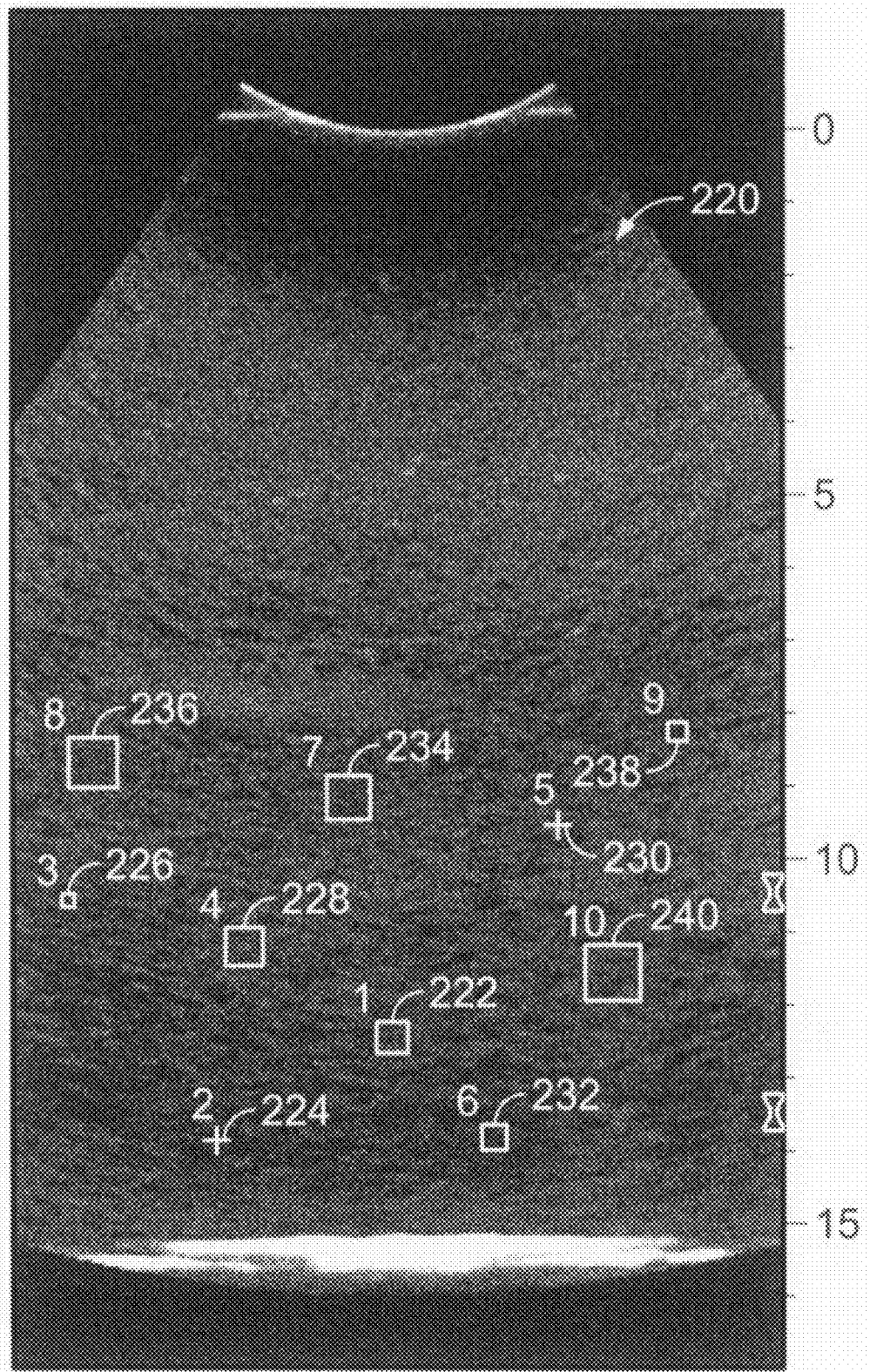
FIG. 6 illustrates an ultrasound image that has multiple image tracking points defined in accordance with an embodiment of the present invention.

FIG. 6 illustrates an ultrasound image 220 that has ten image tracking points defined. As discussed previously, while scanning there is often a need to count the number of points, structures, and/or other items of interest in the body, and it can be difficult to navigate through an organ or other volume in the body and count each occurrence exactly one time. However, by placing an image tracking point on each object or structure as it is found, it is easily determined that the object has already been counted when returning to the object, even if seeing the object from a different view. In such a case, the tracking points can be numbered and/or a numerical total presented to the user to aid in the counting process.

First through tenth tracking points 224-240 are also indicated within the image 220 with numbers, which may be helpful in the case when the user is counting a total number of lesions. The second and fifth tracking points 224 and 230 are in the current imaging or display plane, and thus are indicated by "+" sign in-plane indicators. The third and fourth tracking points 226 and 228, and the sixth through tenth tracking points 232-240 are indicated by out-of-plane indicators that are squares. The size of each square provides additional information to the user regarding the location in space of each of the tracking points with respect to the current image. Large squares, such as the eighth and tenth tracking points 236 and 240, may be further away from the current imaging plane compared to smaller squares, such as the third and ninth tracking points 226 and 238.

Color may also provide positional information to the user. The "+" and associated numbers of the second and fifth tracking points 224 and 230 may be displayed in a first color, such as green, to indicated tracking points within the current image. The square and number of the first tracking point 224 may be indicated with a second color, such as blue, to indicate that the first tracking point 224 is located to a first side of the current image. The squares and numbers of the third, fourth, and sixth through tenth tracking points 226, 228, 232-240 may be indicated with a third color, such as yellow, to indicate that the tracking points are located to a second side of the current image. Also, to provide further positional cues to the user, the image tracking module 124 may indicate the spatial locations of image tracking points with respect to the current image with other colors, graphical indicators, and changes in the display.

Therefore, if the user wishes to view the lesion or structure associated with the eighth tracking point 236, the user may move the probe 106 and the image tracking module 124 automatically updates the sizes, colors, and/or type of indicator for each of the graphical indicators currently displayed on the display 118. For example, the image tracking module 124 may compare a spatial location associated with each of the first through tenth tracking points 224-240 to spatial locations within the current acquisition image or plane, as well as to the spatial detection field as a whole. If the image tracking module 124 determines that a particular tracking point is beyond the current acquisition image, the image tracking module 124 may further determine how far the image tracking point is from the current acquisition image and the direction the image tracking point is located within respect to the current acquisition image. If multiple images are displayed on the display 118, such as three orthogonal planes, the graphical indicators are updated on each of the planes with respect to the particular image plane.

The user monitors the square associated with the eighth tracking point 236, watching for the square to become smaller as the eighth tracking point 236 nears the current acquisition image. Once the eighth tracking point 236 is in-plane, or within the current acquisition image, the image tracking module 124 replaces the associated square with the "+" sign and changes the color to the color designated for in-plane indicators. It should be understood that the above applies equally to when a user moves through a previously acquired volume or moves within frozen image data.

Optionally, when a volumetric image is being displayed, the image tracking points may be embedded in the rendering. Also, if multiple image planes are displayed on the display 118, such as in multiple image or view ports, the image tracking points may be projected onto all of the images.

Also, the user may replace one or more previous tracking points with a single image tracking point, drag or move an image tracking point to a different position, or may add additional tracking points that may be uniquely identified by a different and/or additional graphical indicator, such as a label. Labels may be entered by the user or one or more standard labels may be provided to the user for selection.

The image tracking points may be hidden or removed from the display 118 without losing the associated data. For example, as image tracking points are identified and displayed on the display 118, the current image may become cluttered and difficult to view. The user may choose to remove all or a portion of the image tracking points from the display 118. The user may also redisplay some or all of the image tracking points. Also, the user may clear or delete one, several, or all of the image tracking points.

Image tracking points are also useful to guide the user back to a desired point of interest. When a structure is noted in a 2D, 3D or 4D image, the structure is marked with the tracking point as previously discussed. When the probe 106 is moved to a new location and/or rotated, the tracking point helps to guide the user back to the point of interest. This is helpful to assure that the same point of interest is identified in the new view and is also helpful to improve productivity.

Similarly, the image tracking points assist the user to return to one or more points of interest after performing other actions. For example, during a procedure using contrast, if structure or anatomy of importance is noted during the wash-in of a contrast agent, an image tracking point may be used to identify the location. Then, after imaging other areas of the patient 126, the marked area may be returned to quickly and confidently via the image tracking point later in the contrast cycle or at any other point during the exam.

Figure 7:
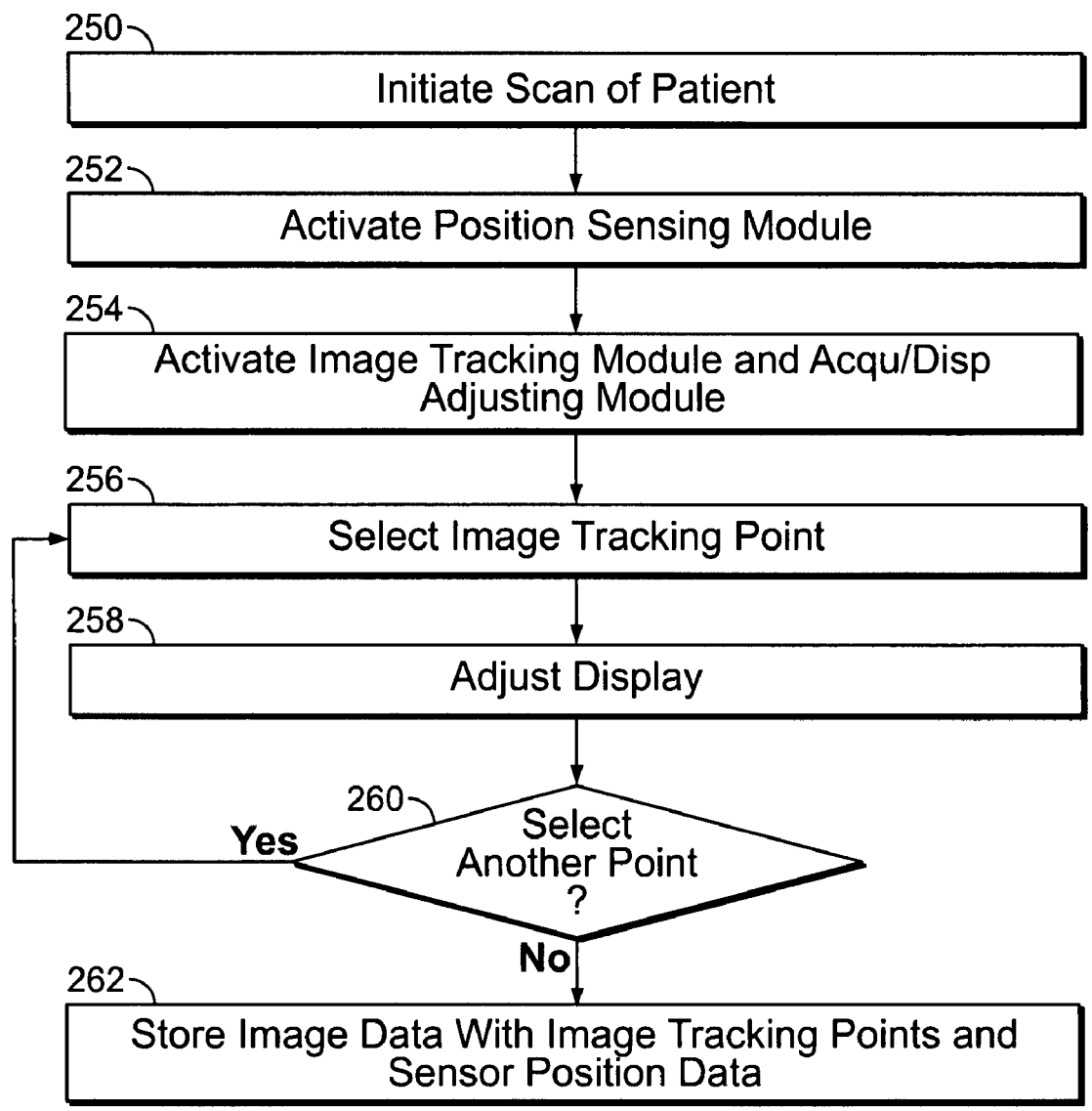
FIG. 7 illustrates a method for adjusting a displayed ultrasound image based on image tracking points in accordance with an embodiment of the present invention.

FIG. 7 illustrates a method for adjusting a displayed ultrasound image based on image tracking points. In this example, the probe 106 is capable of acquiring volume images and may be referred to as a volume probe. The acquisition/display adjusting module 136 may be within the image tracking module 124 and/or stored separately within the memory 122 (as shown in FIG. 3). Optionally, the acquisition/display adjusting module 136 may be used to adjust scanning parameters such that all of the image tracking points or a selected sub-set of the image tracking points are within the current acquisition image. Also, the acquisition/display adjusting module 136 may be used to change, alter, or otherwise adjust the ultrasound data currently displayed on the display 118 based on the image tracking points and is not limited to displaying the current scanning plane. For example, the acquisition/display adjusting module 136 may be used to create desired images having selected image tracking points there-within from frozen or previously acquired data.

When the probe 106 is a volume probe, the location of the acquired slice or slices may be adjusted such that the point or points of interest are always contained in the current image. As long as the image tracking point remains within the volume range of the probe 106, the point can be maintained in the x, y and/or z plane images. Therefore, the point may be maintained in one plane, two planes, such as the x and y planes, as well as within three planes. The user may toggle the image tracking function on and off using the user interface 120. Optionally, the image tracking module 124 may automatically turn off the tracking based on an amount of motion detected by the position sensor 134 on the probe 106. For example, image tracking may be automatically switched off based on a relatively large amount of motion of the probe, and then image tracking may be turned back on through the user interface 120 or after a period of reduced motion of the probe 106.

At 250, the user initiates the scan of the patient 126 with the ultrasound system 100. At 252, the user activates the position sensing module 130, and at 254, the user activates the image tracking module 124 and the acquisition/display adjusting module 136. At 256, the user selects a first image tracking point using the user interface 120, as previously discussed.

At 258, the acquisition/display adjusting module 136 may adjust the ultrasound image on the display 118 to display one or more images including the image tracking point. The images are not limited to in-plane or current acquisition images, and may be any desired orientation and location within the volume. Optionally, if the user scans patient data such that the image tracking point is beyond the current scanning view, the display 118 may display more than one image wherein one image is the current in-plane acquisition image, and another different image shows the image tracking point. Alternatively, one or more acquisition scan planes 128 may be adjusted, such as by adjusting a scanning angle, area, focus and the like, to keep the image tracking point within the current acquisition image. Therefore, the display 118 may display an in-plane view that may have the image tracking point, or one or more image(s) that are not the current acquisition image showing the image tracking point.

At 260, if the user wishes to select another image tracking point, the method returns to 256. At 258, the acquisition/display adjusting module 136 may adjust the displayed ultrasound image, one or more acquisition scan planes 128, and/or display another image and/or an updated image on the display 118 having both or all of the image tracking points therewithin. Therefore, the displayed plane(s) may automatically be adjusted to include more than one image tracking point. One or more displayed views may not be the current acquisition plane or view.

Therefore, the acquisition plane and/or displayed plane may be selected based on two or more image tracking points. For example, if the user identifies two image tracking points (in other words, defining a line between the two image tracking points), the ultrasound system 100 may be set to automatically adjust scan parameters to adjust the acquisition plane to include the two image tracking points. Depending upon the type of probe 106 being used, a second plane orthogonal to the plane containing the two image tracking points may also be acquired and displayed.

By way of example, this concept may be extended to other shapes, such that a displayed view may be a curved plane extending through more than two image tracking points. If the user identifies three image tracking points, the displayed plane may automatically be adjusted to be a curved plane extending to include the three image tracking points. In this example, the displayed plane is not an acquisition plane. Displaying a curved plane may be useful for visualizing a curved vessel within a single plane of data, or visualizing a needle shaft that extends beyond a single plane.

The user may continue to select additional image tracking points (at 256), and may also delete image tracking points as previously discussed. The acquisition/display adjusting module 136 will continue to adjust the acquisition planes and/or the display planes at 260 based on the image tracking points. The user may also select various display protocols to display additional images or process data to extract desired information.

At 262, the user may choose to store the image tracking points, the sensor position data, as well as the image data, such as in the reference coordinate system module 146. Therefore, the same functions may be performed on cine frames, on recalled images and image clips based on the combined data. Also, data may be transferred, such as over the network 138 directly, wirelessly, over the Internet, by using a portable memory device, and the like. Therefore, the processing and analysis functions may also be performed on a workstation or other location remote from the ultrasound system 100. When accessing saved data, the acquisition parameters cannot be changed; however, the user may choose to identify new image tracking points to create different displayed images, or remove one, some, or all of the previously identified image tracking points. For example, the user may choose a sub-set of image tracking points and the ultrasound system 100 may automatically adjust the image to display a plane including the sub-set of points. The user may also cycle through each point in the volume image, such as by entering the specific number of each point or selecting a key on the user interface 120 that directs the display 118 to the next point. The volume or image may then be displayed with the currently selected point as a focal point. For example, the point may be positioned at the center of a volume rendering or at the center of a multiple-plane orthogonal view. This may be accomplished on stored and/or recalled volumes, and on volumes currently being acquired.

The techniques can be combined with other objects that are calibrated to the same position sensing field. These other objects may include one or more additional ultrasound transducers attached to the same ultrasound system 100 or a different ultrasound system that senses position sensors on probes that are within the spatial detection field of the transmitter 132. For example, the additional sensor tracking module 142 may track an additional sensor on a probe (not shown) that interfaces with the system 100.

Alternatively, the position sensing module 130 may detect an additional sensor on a probe that is acquiring imaging data for a different, separate system (not shown). In this example, positional information, as well as diagnostic imaging data, may be transferred between the system over the network 138 or other direct link. If an image tracking point were indicated on an image acquired by the first probe, the image tracking point may also be indicated on an image acquired by the second probe because the tracking sensor on both of the probes are using the same spatial detection field and coordinate tracking system. Therefore, imaging data may be acquired from multiple directions simultaneously.

Currently, biopsies and other needle procedures may be performed under ultrasound guidance. The needle may be within a guide on the probe 106 or may be free-handed or inserted separate from the probe 106 into the patient 126. Unfortunately, the biopsy needle may be difficult to see in some views and therefore image tracking and the use of tracking points may be useful for biopsy needle guidance. Image tracking points may be used to identify the location of a needle tip or other portion of the needle when detected in the in-plane view. When the needle is separate from the probe 106, after the probe 106 is moved or rotated, a previous imaging position may be achieved by using the tracking point. Also, a tracking point may be used to identify a target point of the biopsy procedure, which is the point that is desirable to reach with the needle tip. For example, the target point may identify a specific nodule. Image tracking points are also useful in cases where motion of the probe 106 causes the image displayed on the display 118 to drift away from the needle, or in the case when another view is desired, such as an orthogonal view of the needle tip. The user may then easily return to the previous view of the needle using the tracking point(s). By way of example, a series of tracking points may be used to mark the location of the needle or may be a line/curve-based indicator.

Figure 8:
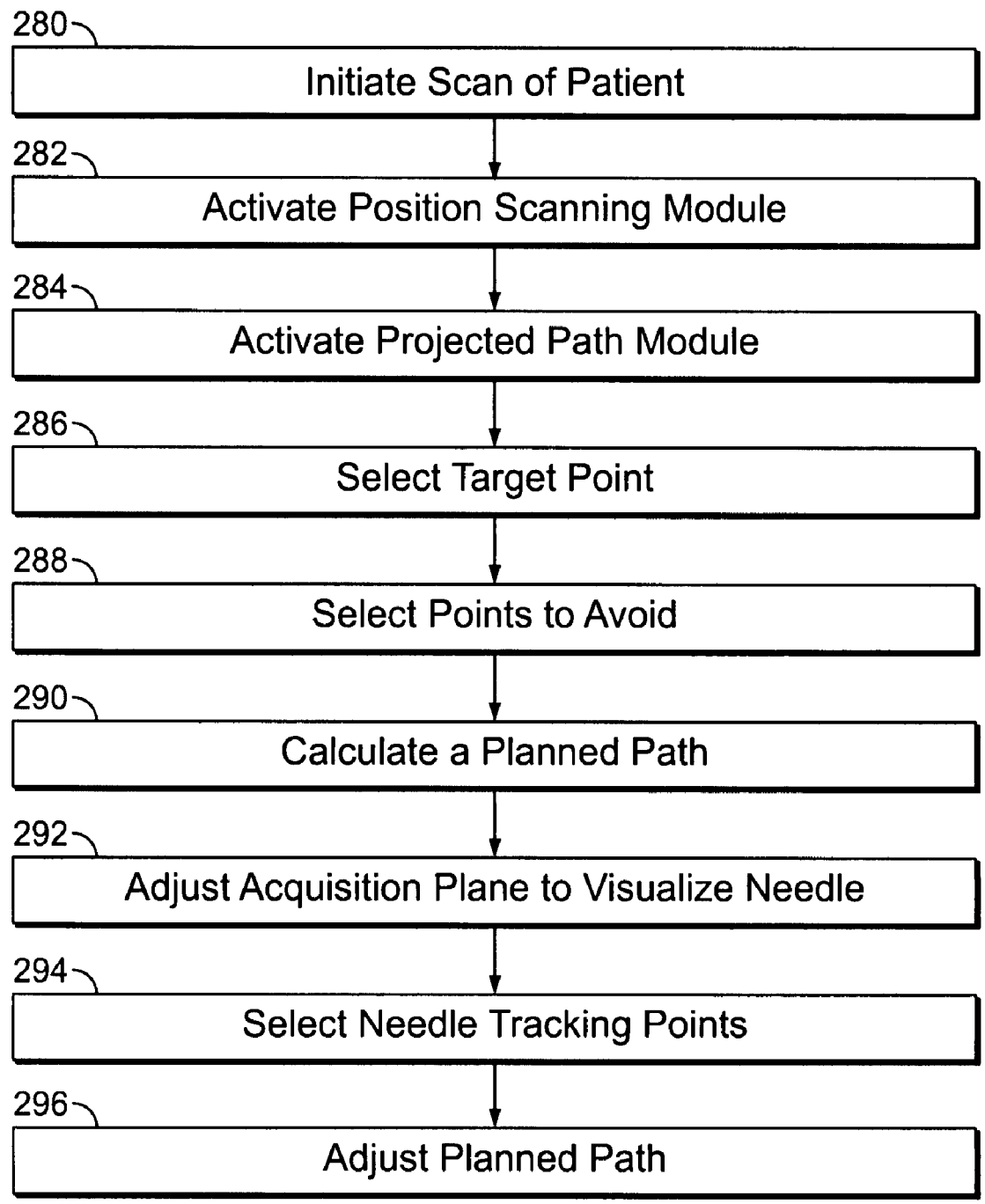
FIG. 8 illustrates a method for using image tracking points during an interventional procedure in accordance with an embodiment of the present invention.

FIG. 8 illustrates a method for using image tracking points during an interventional procedure. The projected path module 140 may be within the image tracking module 124 and/or stored separately within the memory 122 (as shown in FIG. 1). The projected path module 140 helps a user to plan and/or visualize a projected path of a biopsy needle, visualize structures to avoid which may be near to the path, as well as track the needle to help the user guide the needle during the procedure.

Figure 9:
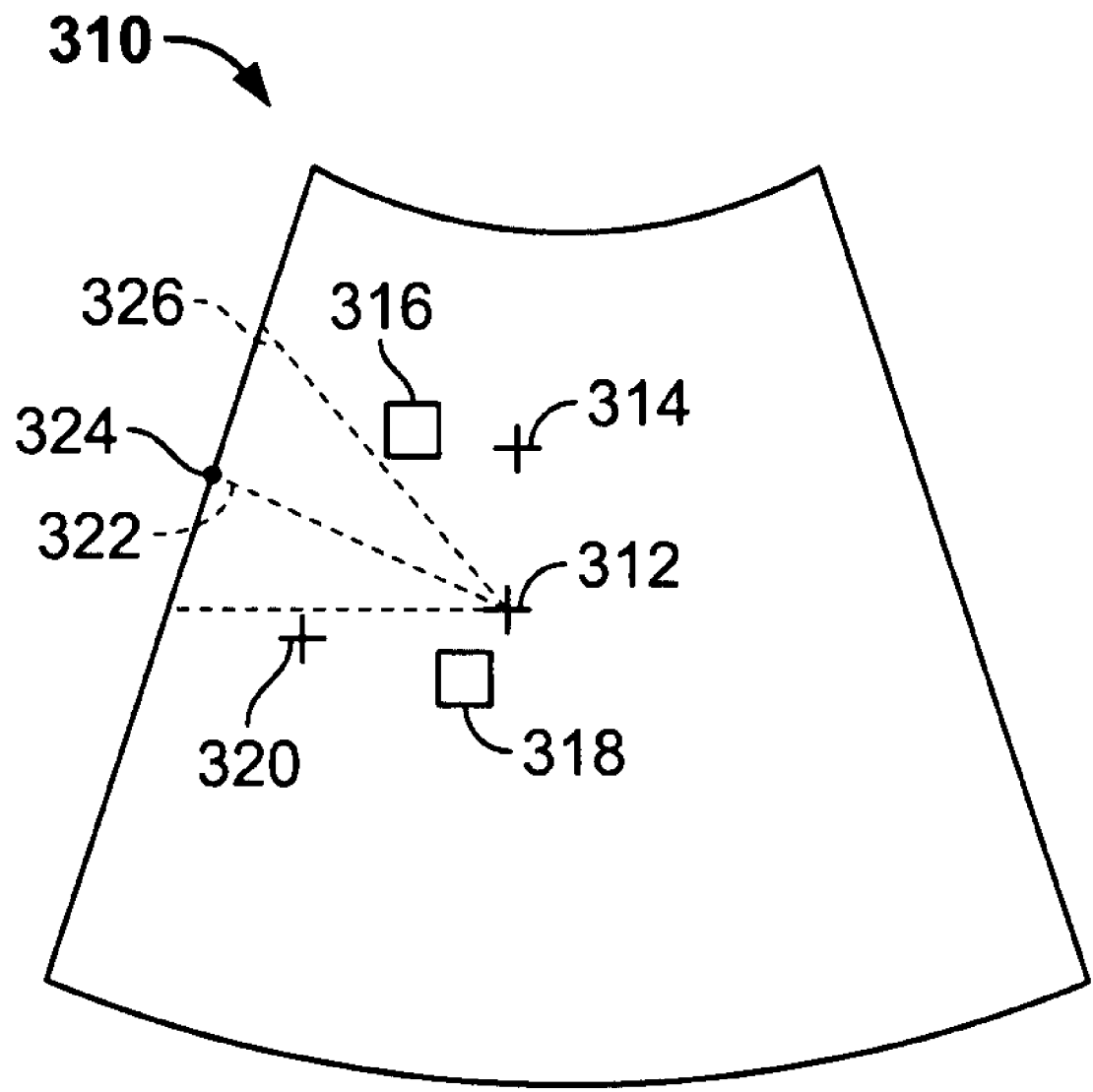
FIG. 9 illustrates an ultrasound image having a planned path displayed thereon for use during an interventional procedure in accordance with an embodiment of the present invention.

At 280, the user initiates the scan of the patient 126 with the ultrasound system 100. FIG. 9 illustrates an ultrasound image 310 used for a biopsy procedure and thus having a planned path displayed thereon. At 282, the user activates the position sensing module 130, and at 284, the user activates the projected path module 140. At 286, the user selects a target point 312 (FIG. 9) to indicate the location of the structure selected for biopsy. It should be understood that the visualizing and selection of image tracking points, target points, and tracking points associated with the needle as discussed below may be performed in any order with respect to each other, and is not limited by the discussion herein.

For example, the user may be viewing a 2D image on the display 118 while placing the target point 312 within the current acquisition image. The user may then rotate and/or move the probe 106 to other views to verify the location of the target point 312, ensuring that the target point 312 is placed within the 3D structure as desired. Optionally, the user may select to display an orthogonal view or other view including the target point 312. The user may reposition the target point 312, such as by using the user interface 120 to select and drag the target point 312 to another location. If multiple images are displayed, the location is updated on all images. The target point 312 may also be used to guide the return of the scanning plane or acquisition image to the original view. Optionally, if a multiplanar or volume probe is used, the multiple simultaneous planes, viewed in 3D, may be used to place the target point 312 in the desired location.

At 288, the user may select one or more other points that indicate points or structure of interest, anatomical landmarks, and/or may be structures to avoid with the needle. Returning to FIG. 9, points 314, 316, 318 and 320 have been identified. Points 314 and 318 are located within the in-plane image 310 and thus are indicated with in-plane indicators "+", and points 316 and 318 are within a different plane and are indicated with out-of-plane indicators such as a square or box. Such points may be nodules, cysts, blood vessels, or any other identified structure. Therefore, tracking points may be used to mark various points or structures in the general planned path of the needle to be avoided. For example, a vessel to be avoided may be marked with various points (or a trace) at the edges of the vessel.

At 290, the projected path module 140 may generate a planned path 322 for the biopsy needle. The planned path 322 allows the user to better identify any objects or structures that are to be avoided that may be near to the needle. Optionally, the user may select a desired needle entry point 324 as an image tracking point, which the projected path module 140 uses when calculating the planned path 322.

The planned path 322 may be indicated with a graphical line or other indication that may be different than how the needle would appear, such as a dotted line. Optionally, a graphical representation such as a tube or cone 326 may indicate a likely range of placement of the needle. The cone 326 may have a graduated diameter based on the distance from the target point 312. Therefore, if the probe 106 is placed perpendicular, or a multi-plane or volume probe 106 is used, the perpendicular plane may display a circular graphical object indicating the potential range of the needle as the needle advances in the patient 126.

The graphics representing the points to avoid that were selected at 288 may be represented such that the points are more noticeable to the user as the points get closer to the planned path 322. For example, if the point is within a predetermined threshold of the planned path 322 and the current acquisition image having the target point 312 defined therein, the point may turn red or have other change in color, and/or flash to indicate that the point to avoid is close to the planned path 322.

The planned path 322 (or cone 326) may be stored and be turned on and off the display 118 while planning, as well as during the actual procedure. For example, the user may display the graphical line, and then change the orientation of the probe 106 to be perpendicular to the plane of the planned path 322. The user may also move the probe 106 to visualize the planned intersection point of the needle based on the planned path 322 through some or all of the perpendicular planes from the needle entry point 324 to the target point 312.

Optionally, a volume of data comprising the area of interest may be acquired prior to the interventional procedure. Then, as image tracking points are noted in the live ultrasound image, the y and z planes that intersect the tracking point or points may be generated from the previously acquired volume and shown on the display 118. These planes may provide additional information and guidance without negatively impacting the acquisition rate, and may eliminate any need to move the probe 106 away from the current acquisition image which is displaying the needle shaft. If a probe 106 capable of fast bi-plane imaging is used, then just the z-plane image may be shown from the previously acquired volume.

At 292, the user may adjust the probe 106 to visualize the needle as the needle enters the patient 126. The user can determine whether the target point 312 and the needle are in line with one another by viewing the geometric relationship of the needle and the target point 312, together with the additional graphical indication of the planned path 322 (which may be the line, cone 326, tube or otherwise shaped graphical indication). If the user determines that the needle shaft and the target point 312 are not within the same plane, it may be determined more easily and earlier during the needle procedure that a directional adjustment is required.

If a line representing the needle is known, then additional capabilities are possible. The needle path may be projected relative to the target point 312 and therefore allow the user to adjust the needle prior to entering into the patient 126. The projection may be made in 3D to assure that the needle is in plane with the target point 312 and is directed along a path to reach the target.

A line representing the needle may be determined manually by entering one or more needle tracking points, determined automatically by sensing positions of one or more sensors on the needle, and/or by automatically detecting the needle. The manual case will be discussed first.

Optionally, at 294, the user may select one or more needle tracking points to be associated with the needle. When a needle is inserted into the patient 126 towards the point of interest or the target point 312, it is difficult to determine by viewing a 2D image whether the needle is in the correct anatomical location, especially in the z dimension. Knowing and documenting the location of the target point 312 in all three planes (x, y, z) is important. Therefore, a needle tip may be marked with an image tracking point. The probe 106 may then be swept through the anatomical area to collect an entire volume of data. The three orthogonal planes (x, y and z) may be displayed simultaneously wherein the tracking point marking the needle tip serves as the intersection point between the three planes. This provides a much clearer view of the anatomical location of the needle tip. The sweep can be achieved via manual movement of the probe 106, mechanical motion or electronically.

The path of the needle may also be used as an intersection line between two planes of a biplane or three-plane view when using a probe capable of volume acquisition or when performing a volume sweep with a standard 2D probe. The intersection point for the third plane may be based on the location of the needle tip. Assuming a needle that is not connected to the probe, even without doing a volume acquisition, by marking the tip of the needle with a needle tracking point, the user can easily adjust the probe 106 to image another plane for a better understanding of the location of the needle tip and then scan back to the original view using the needle tracking point.

Optionally, the user may identify more than one point associated with the needle. For example, as the needle progresses into the patient 126, additional needle tracking points may be identified at a current position of the needle tip and/or along the shaft. The projected path module 140 may then estimate an additional planned path to determine intersection with the target point 312.

At 296, the projected path module 140 may adjust the planned path 322 based on at least the needle tracking point (s). For example, the graphical cone 326 may be updated to better estimate if the needle is going to intersect the target point 312 or if the needle may intersect a point to be avoided.

Turning to the use of additional sensors, one or more position sensors may be used with the needle, together with or in place of, user defined needle tracking points. For example, one or more needle position sensors may be placed along the shaft of the needle, or a single needle position sensor may be placed on the needle and a calibration may be performed to identify the location of the shaft and the tip of the needle with respect to the needle position sensor. When the position sensing module 130 and transmitter 132 are activated, the additional sensor tracking module 142 may also be activated to track the needle position sensor(s) within the spatial detection field as previously discussed with tracking the probe position sensor 134. Also, the user may enter calibration data to define parameters with respect to the needle, such as length of shaft, location of sensor with respect to the needle tip, diameter of the needle shaft, and the like.

Therefore, the additional sensor tracking module 142 may track needle position sensor(s) and/or other additional positional sensors (such as sensors on other probes) within the spatial detection field of the position sensing module 130. For example, an additional needle position sensor may be placed at the tip of the needle (or in a known location relative to the needle tip). The additional sensor tracking module 142 tracks the needle position sensor as a separate and moving needle tracking point. The additional sensor tracking module 142 may track the needle position sensor with respect to the other image tracking points and the current image, showing a projection of the needle position sensor on the current image. Optionally, an additional needle position sensor may be placed proximate to the other end of the needle, such as opposite the needle tip. By tracking two needle position sensors attached to the needle, the acquisition/display adjusting module 136 may automatically update one or more planes, views or images on the display 118 to display the plane of the needle without user adjustment.

By tracking needle position sensor(s), the image tracking module 124 may detect that the needle tip is within a predetermined range of a point to avoid. A warning indication may then be provided to the user. Also, the needle tip, when indicated with a needle position sensor, may be used as the intersection point of a biplane or 3 or more plane view when using a probe 106 capable of multiple plane acquisition or when performing a volume sweep with a standard 2D probe.

Turning to the automatic detection of the needle, optionally, the needle tracking module 144 may be used to automatically detect the presence of the needle in the current image without additional sensors. For example, the needle tracking module 144 may be activated by the user, and the needle tracking module 144 may monitor the ultrasound data for changes indicative of a needle, such as a brightness level suddenly increasing coupled with expected shape/size parameters being satisfied. Other detections may be used. The needle tracking module 144 may automatically place image tracking points along the detected needle so that the user may subsequently move the probe 106, then later return to the imaging plane displaying the needle.

Optionally, the automatically generated image tracking points may be combined with a needle position sensor on the needle (such as at the needle tip or the opposite end with calibration as previously discussed). This additional information associated with the location of the needle may be used to improve the performance of any needle auto-detection algorithm. A live, rendered 3D image of the needle tracking points including those making up the curve of the needle shaft or a line/curve-based indicator of the needle may be displayed on the display 118, overlaid on one or more 2D images that have been properly oriented relative to the needle tracking points, displayed side-by-side with one or more 2D images, or overlaid on a live 3D image rendering. Returning to 296 of FIG. 8, it should be understood that the needle position sensors and the automatic detection of the needle may be used to adjust the planned path 322.

The aforementioned image tracking functionality and features are also useful in RF ablation procedures. For example, the anatomical structures of interest, such as the outline of the tumor being ablated, the location of the needle tip(s), the needle shaft(s) and the planned RF ablation point(s) may be marked, before or during the ablation procedure with imaging tracking points. Once an RF ablation procedure is started, gas is generated that tends to degrade the ultrasound image. The image tracking points or contours that have been marked may be tracked and provide guidance, especially during the time when the RF ablation is reducing or obscuring viewing of the ultrasound image data.

The image tracking points and other tracking features may also be used to combine multiple volumes. Challenges exist in obtaining a volume representation in ultrasound, such as access to the entire volume and the impact of the volume itself on the ultrasound signal. Regarding access, it is difficult to sweep ultrasound beams across the entire volume of interest without encountering obstructions such as air and/or bone which both prevent the ultrasound signal from propagating to the volume of interest. Regarding the impact of the volume itself on the ultrasound signal, tumors and other pathology may greatly reduce through transmission of the ultrasound signal. In these cases, the patient anatomy is scanned from various directions to acquire a complete picture of the volume of interest. Image tracking points may be used to combine these multiple volumes into one volumetric view.

Image tracking points may also be used with volume-guided ultrasound procedures. In volume-guided ultrasound, a previously acquired volume data set is registered with the ultrasound probe 106. The previously acquired volume data set may be an ultrasound data set or from a different imaging modality, such as MR, PET, CT, Nuclear Medicine, and the like. To provide the registration, the position sensing module 130 may be used with one or more position sensors 134 mounted on or in the ultrasound probe 106. Once registered, a slice from the volume is updated in real-time to match the ultrasound image.

Image tracking points may also assist with locating common points in both an ultrasound image or volume and a previously acquired volume data set that may be ultrasound or a different imaging modality. The user may place an image tracking point in the ultrasound image or a previously acquired volume data set. This may be done either before or after the ultrasound image and previously acquired volume data set are registered with each other. Once the volume data set and the live ultrasound image are registered, the projection of the desired point may be shown relative to both the ultrasound image and the previously acquired volume image. In this way, the user may scan to the point of interest with the image tracking point serving as a guide. In practice, the image tracking point can be any point of interest, and may include applications such as marking seed implantation points for treatment applications, such as in oncology, or marking lesions in a CT image that require further investigation using ultrasound. Another example is marking a lesion in CT that is not visible in normal ultrasound, and then using the associated image tracking point as the point of interest while performing a contrast enhanced ultrasound exam.

Thus, diagnostic confidence is improved by confirming that the point of interest from a previously acquired volume of data, potentially of a different modality, is the same point of interest being currently analyzed within a different volume of ultrasound data. Productivity is also enhanced as the region of interest has already been identified from the data in the previously acquired volume prior to the ultrasound exam.

A user may also wish to confirm the accuracy of the registration. When registering volumes of different modalities, in volume-guided ultrasound with the live image registered to the previously acquired volume data set, an image tracking point may be marked in the previously acquired volume and be transferred, and thus projected onto the live ultrasound image. The user locates the actual corresponding point in the body and acquires a plane that includes the image tracking point and the actual point in the body. The user can then visualize or measure the distance between these points as an assessment of the accuracy of the registration.

As discussed previously, the image tracking points may be stored with a volume of data. Then, when an image within the volume is recalled, the image tracking points may again be visualized when manipulating the volume. Additionally, the image tracking points may be projected on a live 2D image once the current image is registered to the previously acquired volume data set. This is helpful for serial studies where the same previously acquired volume may be used multiple times, thus providing confidence that the follow-up study is being done consistently and productively by not needing to reanalyze the previously acquired volume data set.

It should be understood that the image tracking techniques described herein are not limited to ultrasound, and may be applicable to volumes of data acquired by other modalities. For example, a user may view a CT or other volumetric dataset acquired by a different modality. The data may be viewed in slices or planes, similar to the ultrasound images discussed previously. As the user navigates through the volumetric dataset and selects points of interest, the points of interest may be marked with indicators as discussed with respect to FIGS. 4-6, providing the user with visual indication of the relative position of each point of interest to the currently displayed image.

A technical effect of at least one embodiment is selecting image tracking points within a current scanning or acquisition plane, image, volume, and the like. As the user moves the probe to acquire other images, the image tracking points remain on the display, but the graphical representation may be changed based on the relationship of each of the image tracking points to the currently displayed image. The image tracking points allow the user to easily count structures within a body, identify points and anatomy to be avoided during an interventional procedure, as well as visualize and plan a biopsy or other interventional procedure. Additional position sensors may be used to track the needle within the image. Images on the display may be changed based on the image tracking points to ensure that the image tracking points are displayed on at least one image. Also, the scanning parameters may be changed to maintain one or more image tracking points within the current acquisition image or scanning plane. The image tracking points may also be used to combine volumes of data for comparison and to track progress of a patient.

While the invention has been described in terms of various specific embodiments, those skilled in the art will recognize that the invention can be practiced with modification within the spirit and scope of the claims.

What is claimed is:

1. An ultrasound system comprising:
a position sensing module configured for detecting spatial information associated with a volume of data acquired from an ultrasound scan;
a display configured for displaying first and second images based on the volume of data, the first and second images comprising first and second portions of the volume of data, the first and second portions being at least partially different with respect to each other;
a user interface configured for selecting a first image tracking point on the first image, the first image tracking point being indicated on the first image with a first indicator; and
an image tracking module configured for tracking the first image tracking point within the volume of data, the image tracking module indicating on the display a spatial relationship of the first image tracking point to the second image, wherein the image tracking module is further configured for changing an appearance of a graphical indicator associated with the first image tracking point to convey a distance of the first image tracking point to the second image when the first image tracking point is not within the second image, the appearance of the graphical indicator changed by the image tracking module as the distance of the first image tracking point to the second image changes.

2. The system of claim 1, further comprising:
an ultrasound probe configured for transmitting and receiving ultrasound data, the volume of data further comprising the ultrasound data;
a position sensor mounted proximate to the probe; and
the position sensing module further comprising a transmitter for creating a spatial detection field, the position sensor and the probe being within the spatial detection field, the probe acquiring the volume of data within the spatial detection field, the image tracking module tracking the first image tracking point with respect to a current position of the position sensor within the spatial detection field.

3. The system of claim 1, wherein the image tracking module displays the first indicator as a first graphical indicator on the first image, the image tracking module displaying the first indicator as a second graphical indicator on the second image, the first and second graphical indicators being different from each other.

4. The system of claim 1, further comprising:
an ultrasound probe configured for transmitting and receiving ultrasound data, the volume of data further comprising the ultrasound data;
a position sensor mounted proximate to the probe; and
a transmitter mounted proximate to the position sensing module for creating a spatial detection field, the position sensor and the probe being within the spatial detection field, the volume of data being acquired within the spatial detection field, wherein the system being one of a handheld ultrasound device and a hand-carried ultrasound device.

5. The system of claim 1, wherein the display displaying a current acquisition image based on ultrasound data being acquired by the probe, wherein the first image tracking point is spatially located outside of the current acquisition image, the image tracking module assigning first and second colors to the first indicator when the first image tracking point is spatially located in first and second directions, respectively, with respect to the current acquisition image, the first and second colors being different with respect to each other.

6. The system of claim 1, wherein the image tracking module changes at least one of a color, a size, and a graphical representation of the first indicator on the second image based on a relative position of the first image tracking point with respect to the second image.

7. The system of claim 1, wherein the image tracking module associates at least one of a number and a label with the first image tracking point, the display displaying the at least one of a number and a label proximate to the first indicator.

8. The system of claim 1, wherein the image tracking module dynamically changes the appearance of the graphical indicators based on a change in the spatial relationship of the first image tracking point to the second image.

9. A method for tracking structures within a diagnostic imaging dataset, the method comprising:
selecting a first image tracking point within a first image being displayed on a display, the first image being within a volumetric dataset, the volumetric dataset further comprising a reference coordinate system;
displaying a first graphical indicator on the first image associated with the first image tracking point;
tracking a relative position of the first image tracking point with respect to a subsequent image being displayed on the display, the relative position being based on the reference coordinate system;
displaying a second graphical indicator on the subsequent image based on the relative position of the first image tracking point to the subsequent image; and
changing an appearance of graphical indicators associated with each of the image tracking points to convey a distance of the first image tracking point to the second image when the first image tracking point is not within the second image, the appearance of the graphical indicator changed by the image tracking module as the distance of the first image tracking point to the second image changes.

10. The method of claim 9, further comprising displaying a second image on the display based on at least the first image tracking point, the first and second images being different with respect to each other.

11. The method of claim 9, further comprising:
acquiring a current acquisition image; and
adjusting at least one acquisition parameter associated with the current acquisition image to display the first image tracking point within the current acquisition image.

12. The method of claim 9, wherein the volumetric dataset is one of frozen, currently being acquired, and previously acquired.

13. The method of claim 9, further comprising:
selecting a target point within the first image;
projecting a planned path to the target point;
displaying the planned path on the first image; and
displaying a graphical indicator on the first image based on the relative position of the first image tracking point to the planned path.

14. The method of claim 9, further comprising toggling the first graphical indicator on and off the display.

15. The method of claim 9, further comprising:
acquiring a current acquisition image;
projecting a planned path for a needle based on at least one image tracking point;
detecting the needle within the current acquisition image; and
adjusting the planned path based on a position of the needle relative to the at least one image tracking point.

16. The method of claim 9, further comprising:
selecting first and second points of interest within a previously acquired volume;
selecting third and fourth points of interest within the volumetric dataset, the first and second points of interest corresponding to the third and fourth points of interest, respectively; and
registering the previously acquired volume and the diagnostic imaging dataset based on the first and second points of interest.

17. An ultrasound system comprising:
a position sensing module comprising a transmitter configured for creating a spatial detection field;
a position sensor mounted on an ultrasound probe, the position sensor providing positional information with respect to the probe within the spatial detection field, the probe acquiring at least a current acquisition image comprising ultrasound data;
a display configured for displaying image tracking points within the ultrasound data; and
an image tracking module configured for tracking the image tracking points with respect to the position sensor and the current acquisition image, the image tracking module further configured for changing an appearance of graphical indicators associated with each of the image tracking points to convey a distance of the image tracking points to the current acquisition image when the image tracking points are not within the current acquisition image, the appearance of the graphical indicator changed by the image tracking module as the distance of the image tracking points to the current acquisition image changes.

18. The system of claim 17, further comprising:
a user interface configured for selecting at least one needle tracking point; and
a projected path module projecting a needle path within the ultrasound data based at least on the at least one needle tracking point.

19. The system of claim 17, further comprising:
a user interface configured for selecting a target point and an interventional entry point; and
a projected path module configured for generating a planned path based at least on the interventional entry point and the target point, the projected path being displayed on the display, the image tracking module changing the indicator associated with the first image tracking point when a first image tracking point is one of within the planned path and within a predetermined proximity of the planned path.

20. The system of claim 17, further comprising a needle sensor mounted on a biopsy needle, the position sensing module detecting a position of the needle sensor within the spatial detection field, the image tracking module changing the graphical indicator of a first image tracking point when the first image tracking point is within a predetermined proximity of the needle sensor.

21. The system of claim 17, wherein the system is one of a portable, handheld and hand carried system.

* * * * *